United States Patent
Mo et al.

(10) Patent No.: US 11,309,703 B2
(45) Date of Patent: Apr. 19, 2022

(54) TRANSFORMER SIMULATION SYSTEM, AND SIMULATION AND MEASUREMENT METHOD FOR SETTING VALUE

(71) Applicant: GUANGZHOU POWER SUPPLY CO., LTD., Guangzhou (CN)

(72) Inventors: Wenxiong Mo, Guangzhou (CN); Yong Wang, Guangzhou (CN); Qingdan Huang, Guangzhou (CN); Haoyong Song, Guangzhou (CN); Yuqing Chen, Guangzhou (CN); Wei Wang, Guangzhou (CN); Zhuya Li, Guangzhou (CN); Chongzhi Zhao, Guangzhou (CN); Jing Liu, Guangzhou (CN); Liqiang Pei, Guangzhou (CN); Yaru Zhang, Guangzhou (CN); Binbin He, Guangzhou (CN); Peiwei Wu, Guangzhou (CN); Qin Xu, Guangzhou (CN); Hui Zeng, Guangzhou (CN)

(73) Assignee: GUANGZHOU POWER SUPPLY CO., LTD., Guangzhou (CN)

( * ) Notice: Subject to any disclaimer, the term of this patent is extended or adjusted under 35 U.S.C. 154(b) by 260 days.

(21) Appl. No.: 16/608,011

(22) PCT Filed: Sep. 30, 2018

(86) PCT No.: PCT/CN2018/109164
§ 371 (c)(1),
(2) Date: Oct. 24, 2019

(87) PCT Pub. No.: WO2020/051961
PCT Pub. Date: Mar. 19, 2020

(65) Prior Publication Data
US 2021/0336433 A1    Oct. 28, 2021

(30) Foreign Application Priority Data

Sep. 13, 2018   (CN) .......................... 201811068880.0

(51) Int. Cl.
*H02H 7/04* (2006.01)
*G01F 1/00* (2006.01)
(Continued)

(52) U.S. Cl.
CPC ................. *H02H 7/04* (2013.01); *G01F 1/00* (2013.01); *H02H 6/00* (2013.01); *G01N 33/2841* (2013.01)

(58) Field of Classification Search
CPC ... H02H 7/04; H02H 6/00; G01F 1/00; G01N 33/2841
See application file for complete search history.

(56) References Cited

U.S. PATENT DOCUMENTS

| 3,816,801 A | * | 6/1974 | Almand, III | ..... G01R 19/16509 |
| | | | | 361/37 |
| 2012/0197559 A1 | * | 8/2012 | Nagao | .................. G01N 33/287 |
| | | | | 702/58 |

(Continued)

FOREIGN PATENT DOCUMENTS

| CN | 201732147 U | 2/2011 |
| CN | 102889906 A | 1/2013 |

(Continued)

OTHER PUBLICATIONS

Maruyama et al., "Temperature Stabilization of Pulsating Flow in High Pressure Field using Coaxial Tube Heat Exchanger with Liquid Oil Tuner", Jul. 30, 2012, Published by the 10th international energy conversion engineering conference and American Institute of Aeronautics and Astronautics (Year: 2012).*

(Continued)

*Primary Examiner* — Peter J Macchiarolo
*Assistant Examiner* — John M Royston

(57) ABSTRACT

A transformer simulation system and a measurement method for setting value simulation are disclosed. The transformer (Continued)

simulation system includes an oil tank, a heating device, a pump body, a first oil pipe, a second oil pipe and a first flow sensor. The heating device is disposed in the oil tank. The oil tank is provided with a first inlet and a first outlet, the first outlet is connected to the first oil pipe, and the first inlet is connected to the second oil pipe. An end of the first oil pipe away from the oil tank is a first mounting end for being connected to an oil inlet of a gas relay, and an end of the second oil pipe away from the oil tank is a second mounting end for being connected to an oil outlet of the gas relay. The pump body is connected to the first oil pipe or the second oil pipe, and the first flow sensor is disposed in the first oil pipe. The above-described transformer simulation system can measure the oil flow velocity, that is the setting value of the gas relay, and the type of the insulation oil in the oil tank can be replaced, then the corresponding setting value of the gas relay is obtained, so as to prevent the original gas relay from not playing the role of the protection due to a different property of the insulation oil.

10 Claims, 1 Drawing Sheet

(51) Int. Cl.
*H02H 6/00* (2006.01)
*G01N 33/28* (2006.01)

(56) References Cited

U.S. PATENT DOCUMENTS

2012/0247204 A1* 10/2012 Herz ................ G01N 33/2841
                                                                  73/431
2018/0259451 A1*  9/2018 Buijs ....................... H01F 27/12

FOREIGN PATENT DOCUMENTS

| CN | 202938496 U | 5/2013 |
| CN | 102889906 B | 7/2014 |
| CN | 204197309 U | 3/2015 |
| CN | 104569652 A | 4/2015 |
| CN | 107084803 A | 8/2017 |
| CN | 207602111 U | 7/2018 |
| CN | 108375727 A | 8/2018 |
| WO | 2011/101013 A1 | 8/2011 |

OTHER PUBLICATIONS

First Office Action, dated Aug. 5, 2019, issued in Chinese Application No. 201811068880.0, filed Sep. 13, 2018, 19 pages.
International Search Report PCT of PCT/CN2018/109164, filed Sep. 30, 2018, 5 pages.
Search Report issued in Chinese Application No. 201811068880.0, filed Sep. 13, 2018, 1 page.
Extended European Search Report dated Sep. 30, 2018, issued in corresponding European Application No. EP 18914931.3, filed Mar. 24, 2020, 7 pages.
Second Chinese Office Action dated Jun. 8, 2020, issued in corresponding Chinese Application No. 201811068880.0, filed Sep. 13, 2018, 15 pages.
International Search Report dated Jun. 12, 2019, issued in corresponding International Application No. PCT/CN2018/109164, filed Sep. 30, 2018, 2 pages.

* cited by examiner

TRANSFORMER SIMULATION SYSTEM, AND SIMULATION AND MEASUREMENT METHOD FOR SETTING VALUE

CROSS REFERENCE TO RELATED APPLICATIONS

This application is a national stage for International Application PCT/CN2018/109164, filed on Sep. 30, 2018, which claims the priority benefits of Chinese Patent Application No. 201811068880.0, titled "TRANSFORMER SIMULATION SYSTEM, AND SIMULATION AND MEASUREMENT METHOD FOR SETTING VALUE" and filed on Sep 13, 2018. The entireties of these applications are incorporated by reference herein for all purposes.

TECHNICAL FIELD

The present disclosure relates to power grid test equipment, and in particular, to a transformer simulation system and a simulation and measurement method for a setting value.

BACKGROUND

Heavy gas protection is a main protection when an internal fault occurs inside a transformer. When a fault occurs inside an oil-immersed transformer, an insulation material is decomposed by an electric arc and a large amount of gas is generated. The gas flows from the oil tank to the oil conservator through a gas relay. When the oil flow velocity reaches a setting value, the heavy gas activates a protection action.

The traditional oil-immersed transformer uses mineral insulation oil as insulation liquid. With the development of the transformer, the type of the insulation liquid is also developing in the direction of environment-friendly and cleaning. But since the properties of the new type insulation liquid are greatly different from the mineral insulation oil, when the oil-immersed transformer using a new insulation liquid malfunctions, the oil flow velocity will change. If the setting value is still referenced to the previous value, the heavy gas protection for the transformer cannot be performed in time, which will result in equipment damage and potential safety hazards.

SUMMARY

Based on above, an objective of present disclosure is to provide a transformer simulation system and a simulation and measurement method for a setting value, which are capable to determine a setting value of a gas relay, overcoming the deficiencies of the prior art.

The technical solutions are described below.

A transformer simulation system is provided, including an oil tank, a heating device, a pump body, a first oil pipe, a second oil pipe and a first flow sensor. Said heating device is disposed in said oil tank. Said oil tank is provided with a first inlet and a first outlet. Said first outlet is connected to said first oil pipe, and said first inlet is connected to said second oil pipe. An end of said first oil pipe away from said oil tank is a first mounting end for being connected to an oil inlet of a gas relay, and an end of said second oil pipe away from said oil tank is a second mounting end for being connected to an oil outlet of the gas relay. Said pump body is connected to said first oil pipe or said second oil pipe. Said first flow sensor is disposed in said first oil pipe.

In the above transformer simulation system, the oil inlet of the gas relay is connected to the first oil pipe, and the oil outlet of the gas relay is connected to the second oil pipe. Then the pump body is activated, so that the oil in the oil tank is sequentially circulated among the first oil pipe, the gas relay and the second oil pipe. The heating device can heat the oil in the oil tank, so as to simulate the oil temperature as the temperature at the transformer fault. Thus, the flow condition of the oil at the transformer fault can be simulated, and the oil flow velocity in the first oil pipe can be measured by the first flow sensor. Since the oil flow velocity increases and reaches the setting value of the gas relay when the transformer malfunctions, the protection action of the gas relay can be triggered. As a result, the above transformer simulation system can simulate the environment at the transformer fault, and the oil flow velocity can be measured, that is, the setting value of the gas relay can be obtained. The type of the insulation oil in the oil tank can be changed, and the corresponding setting value of the gas relay can be obtained, so as to prevent the original gas relay from not playing the role of the protection due to a different property of the insulation oil, after the insulation oil type is changed.

Further, said heating device includes a heat source, a turbine wheel and a driver. Said turbine wheel has a vertically disposed axis. Said turbine wheel is disposed opposite to said heat source. Said driver is used to drive the turbine wheel to rotate.

Further, the above transformer simulation system further includes a third oil pipe, a fourth oil pipe and a second flow sensor. Said oil tank is further provided with a second inlet and a second outlet. Said third oil pipe is connected to said second outlet. Said fourth oil pipe is connected to said second inlet. An end of said third oil pipe away from said oil tank and an end of said fourth oil pipe away from said oil tank are both used to connect to said gas relay. An inner diameter of said first oil pipe is greater than an inner diameter of said third oil pipe. Said second oil pipe and said fourth oil pipe are both provided with a switch control valve, and said second flow sensor is disposed in said third oil pipe.

Further, said second oil pipe includes a first branch pipe and a second branch pipe. An end of said first branch pipe is said second mounting end, an end of said second branch pipe is connected to said first inlet, and another end of said first branch pipe and another end of said second branch pipe are respectively connected to said pump body. The fourth oil pipe includes a third branch pipe and a fourth branch pipe, an end of said third branch is connected to the gas relay, and another end of said third branch is connected to said first branch pipe. An end of said fourth branch pipe is connected to said second inlet, and another end of said fourth branch is connected to said second branch pipe.

Further, a temperature probe for detecting oil temperature is disposed in said oil tank, and said temperature probe is disposed at said first outlet.

Further, the above transformer simulation system further includes a temperature sensor disposed in said first mounting end.

Further, said first mounting end and said second mounting end are both disposed to be inclined with respect to a horizontal plane. A central axis of said first mounting end and a central axis of said second mounting end are disposed in a same direction. Said first mounting end is lower than said second mounting end in a vertical direction.

Further, said heating device has a heating temperature in a range from 50° C. to 80° C.

Further, a pressure sensor for detecting oil pressure is provided in said oil tank.

A simulation and measurement method for a setting value simulation is also provided, which uses the above transformer simulation system, and includes:

connecting the oil inlet of gas relay to said first mounting end, and connecting the oil outlet of gas relay to said second mounting end;

activating said pump body, and setting a power of said pump body as a normal power of transformer;

setting said heating temperature of said heating device as an oil temperature at transformer fault; and measuring a flow velocity in said first oil pipe according to said first flow sensor, as the setting value.

According to the above simulation and measurement method for a setting value simulation, after the gas relay is connected to the first oil pipe and the second oil pipe respectively, the power of the pump body is set to a normal power of the transformer (i.e., the power during normal operation of the transformer), and the heating temperature of the heating device is set to the oil temperature of the transformer fault (i.e., the oil temperature at the time that the transformer malfunctions). Thus, the internal environment of the transformer at the transformer fault can be simulated. Thus, the flow velocity in the first oil pipe measured by the first flow sensor is the oil flow velocity at the transformer fault. Then the setting value of the gas relay is obtained. When a different type of insulation oil is put into the oil tank, the corresponding setting value of the gas relay can be obtained, so as to prevent the original gas relay from not playing the role of the protection due to a different property of the insulation oil, after the type of the insulation oil is changed.

DESCRIPTION OF THE REFERENCE SIGNS

Figure 1:
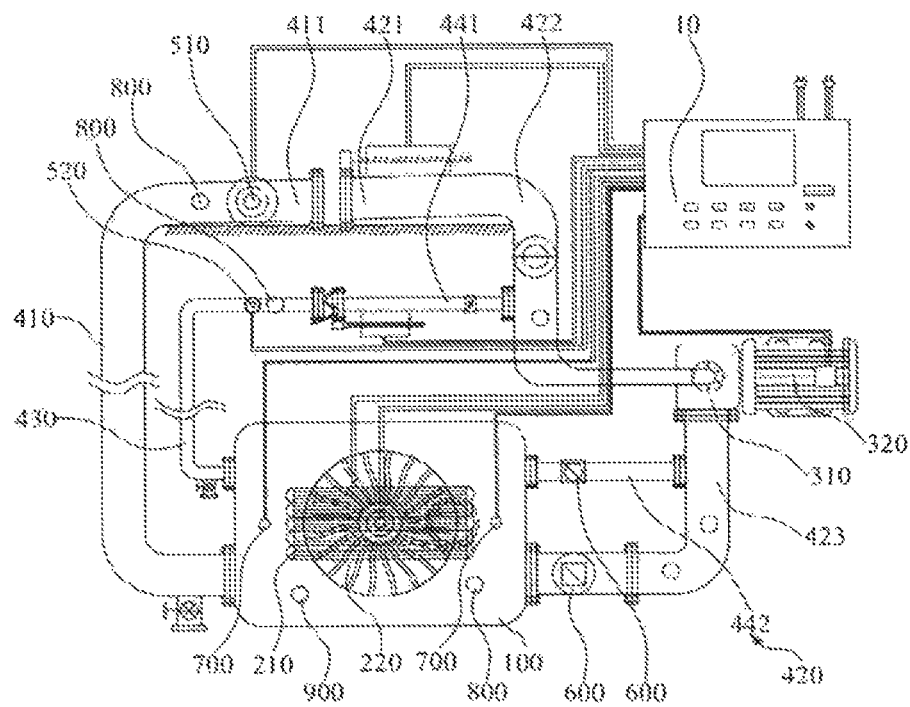
FIG. 1 is a schematic structural diagram illustrating a transformer simulation system according to an embodiment of the present disclosure.

100: oil tank; 110: oil gauge; 200: heating device; 210: heat source; 220: turbine wheel; 230: driver; 300: pump body; 310: mounting cavity; 320: motor; 410: first pipe; 411: first mounting end; 420: second oil pipe; 421: second mounting end; 422: first branch pipe; 423: second branch pipe; 430: third oil pipe; 440: fourth oil pipe; 441: third branch pipe; 442: fourth branch pipe; 510: first flow sensor; 520: second sensor; 600: switch control valve; 700: temperature probe; 800: temperature sensor; 900: pressure sensor; and 10: controller.

DETAILED DESCRIPTION

In order to facilitate the understanding of the present disclosure, the present disclosure will be described more fully hereinafter with reference to the accompanying drawings. Preferred embodiments of the present disclosure are given in the drawings. However, the present disclosure may be embodied in many different forms and is not limited to the embodiments described herein. Rather, the objective of these embodiments provided is to make the present disclosure to be understood more comprehensive.

It should be noted that when an element is referred to as being "fixed" to another element, it may be directly on the other element or an intervening element may be present. When an element is considered as being "connected" to another element, it may be directly connected to the other element or an intervening element may be present respectively. The terms "vertical", "horizontal", "left", "right", and the like, as used herein, are for the purpose of illustration and are not intended to represent the only embodiment.

All the technical and scientific terms used herein have the same meaning as commonly understood by those skilled in the art to which this disclosure belongs, unless otherwise defined. The terminology used in the description of the present disclosure is for the purpose of describing particular embodiments and is not intended to limit the disclosure. The term "and/or" as used herein includes any and all combinations of one or more of the associated listed items.

The terms "first" and "second" in the present disclosure do not represent a specific number and order, but are merely used for distinguishing names.

In this specific embodiment, the oil tank may be filled with environment-friendly insulation oil such as plant insulation oil or synthetic ester insulation oil, or mineral insulation oil, and the like.

As shown in FIG. 1, a transformer simulation system is disclosed in an embodiment. The transformer simulation system includes an oil tank 100, a heating device 200, a pump body 300, a first oil pipe 410, a second oil pipe 420, and a first flow sensor 510. The heating device 200 is disposed in the oil tank 100. The oil tank 100 is provided with a first inlet and a first outlet, the first outlet is connected to the first oil pipe 410, and the first inlet is connected to the second oil pipe 420. An end of to the first oil pipe 410 away from the oil tank 100 is a first mounting end 411 for being connected to the oil inlet of a gas relay, and an end of the second oil pipe 420 away from the oil tank 100 is a second mounting end 421 for being connected to the oil outlet of the gas relay. The pump body 300 is connected to the first oil pipe 410 or the second oil pipe 420, and the first flow sensor 510 is disposed in the first oil pipe 410.

In the above transformer simulation system, the oil inlet of the gas relay is connected to the first oil pipe 410, and the oil outlet of the gas relay is connected to the second oil pipe 420. Then the pump body 300 is activated, so that the oil in the oil tank 100 is sequentially circulated among the first oil pipe 410, the gas relay and the second oil pipe 420. The heating device 200 can heat the oil in the oil tank, so as to simulate the oil temperature as the one at the transformer fault. Thus, the flow condition of the oil at the transformer fault can be simulated, and the oil flow velocity in the first oil pipe 410 can be measured by the first flow sensor 510. Since the oil flow velocity increases and reaches the setting value of the gas relay when the transformer malfunctions, the protection action of the gas relay can be triggered. As a result, the above transformer simulation system can simulate the environment at the transformer fault, and the oil flow velocity can be measured, that is, the setting value of the gas relay can be obtained. The type of the insulation oil in the oil tank 100 can be changed, and the corresponding setting value of the gas relay can be obtained, so as to prevent the original gas relay from not playing the role of the protection due to the different properties of the insulation oil, after the insulation oil type is changed.

In this embodiment, the "oil flow velocity" is the flow velocity of the insulation oil in the oil tank 100 flowing in the pipe.

When the type or temperature of the insulation oil changes, the viscosity or other properties of the insulation oil may change, which then affects the oil flow velocity. Therefore, in order to better simulate the flow condition of the insulation oil at the transformer fault, a heating device 200 is disposed in the oil tank 100, which is used to heat the insulation oil.

Optionally, the above transformer simulation system further includes a controller 10 that is electrically connected to the pump body 300, the heating device 200 and the first flow sensor 510, respectively. The controller 10 is pre-input with the power of the pump body 300 and the heating temperature of the heating device. The controller 10 receives the oil flow velocity measured by the first flow sensor 510.

Optionally, a display screen for displaying data is provided on the controller 10. The data that can be displayed on the display screen includes the oil flow velocity, the heating temperature, the power of pump body 300 and so on.

Specifically, the end portions of the first mounting end 411 and the second mounting end 421 are both provided with a mounting flange for matching the gas relay respectively. In this case, it can facilitate the installation of the gas relay to ensure that the gas relay remains stable during operation.

Figure 2:
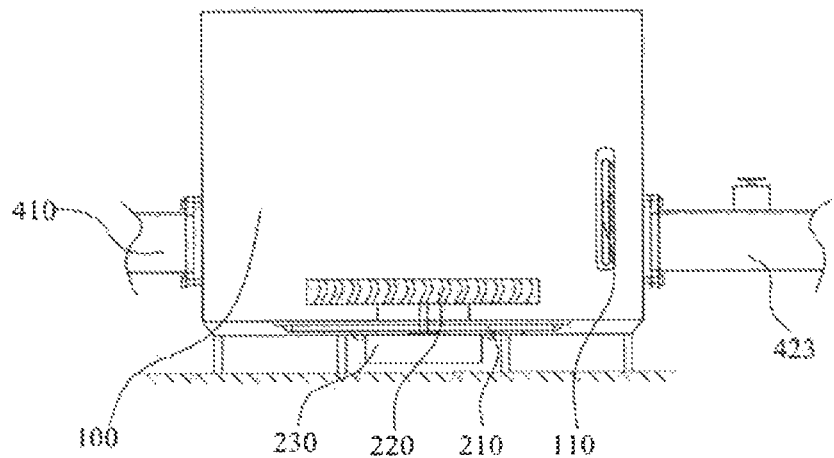
FIG. 2 is a partial cross-sectional view of a transformer simulation system according to an embodiment of the present disclosure.

Further, as shown in FIG. 1 and FIG. 2, the heating device 200 includes a heat source 210, a turbine wheel 220 and a driver 230. An axis of the turbine wheel 220 is vertically disposed, and the turbine wheel 220 is disposed opposite to the heat source 210. The driver 230 is used to drive the turbine wheel 220 to rotate. By the rotation of the turbine wheel 220, the heat generated by the heat source 210 can be diffused to allow the oil temperature in the oil tank 100 uniform, and then the temperature of the oil entering the first oil pipe 410 can be prevented from being non-uniform which affects the measurement of the setting value of the gas relay.

Optionally, the heat source 210 is disposed at the bottom of the oil tank 100, the turbine wheel 220 is disposed above the heat source 210, and a central axis of the turbine wheel 220 is disposed in a vertical direction. Since the heated insulation oil will rise, the heat source 210 disposed at the bottom of the oil tank 100 can continuously heat the insulation oil with a lower temperature. Meanwhile the temperature exchange between the insulation oils at different temperatures can be accelerated by the rotation of the turbine wheel 220 to further allow the oil temperature distribution in the oil tank 100 uniform. It can better simulate the condition of the insulation oil at the transformer fault. The heat source 210 disposed at the bottom of the oil tank 100 prevents the heat source 210 from being burned to cause a safety accident.

Specifically, the heat source 210 is a heating wire that is bent in an "S" shape. So that the heat exchange with the insulation oil is faster to better simulate the heating condition of the insulation oil at the transformer fault.

Optionally, as shown in FIG. 2, an oil gauge 110 is further disposed in the oil tank 100, and the oil gauge 110 is used to measure the volume of the insulation oil in the oil tank 100.

Further, as shown in FIG. 1, the above transformer simulation system further includes a third oil pipe 430, a fourth oil pipe 440, and a second flow sensor 520. The oil tank 100 is further provided with a second inlet and a second outlet. The third oil pipe 430 is connected to the second outlet, and the fourth oil pipe 440 is connected to the second inlet. An end of the third oil pipe 430 away from the oil tank 100, and an end of the fourth oil pipe 440 away from the oil tank 100 are both used to connect to the gas relay. The inner diameter of the first oil pipe 410 is greater than the inner diameter of the third oil pipe 430. The second oil pipe 420 and the fourth oil pipe 440 are both provided with a switch control valve 600, and the second flow sensor 520 is disposed in the third oil pipe 430. In this case, since the inner diameters of the first oil pipe 410 and the third oil pipe 430 are different, it can be used to detect the setting values of the gas relays with different specifications. When it is necessary to use the first oil pipe 410 and the second oil pipe 420 to perform the setting value detection of the gas relay, the switch control valve 600 in the fourth oil pipe 440 can be turned off. Similarly, when the third oil pipe 430 and the fourth oil pipe 440 are required to perform the setting value detection of the gas relay, the switch control valve 600 in the second oil pipe 420 can be turned off.

Optionally, the inner diameter of the first oil pipe 410 is 80 mm, and the inner diameter of the third oil pipe 430 is 25 mm. The gas relays that match the pipes of the above specifications are common and can be easy to use. In addition, the first oil pipe 410 and the second oil pipe 420 may be set to other sizes. Specifically, the inner diameter of the first oil pipe 410 matches the inner diameter of the second oil pipe 420, and the inner diameters of the third oil pipe 430 matches the inner diameter of the fourth oil pipe 440. The size of the switch control valve 600 in the second oil pipe 420 matches the inner diameter of the second oil pipe 420. The size of the switch control valve 600 in the fourth oil pipe 440 matches the inner diameter of the fourth oil pipe 440.

Further, as shown in FIG. 1, the second oil pipe 420 includes a first branch pipe 422 and a second branch pipe 423. One end of the first branch pipe 422 is the second mounting end 421, and one end of the second branch pipe 423 is connected to the first inlet. The other end of the first branch pipe 422 and the other end of the second branch pipe 423 are respectively connected to the pump body 300. The fourth oil pipe 440 includes a third branch pipe 441 and a fourth branch pipe 442. One end of the third branch pipe 441 is used to connect to the gas relay, and the other end of the third branch pipe 441 is connected to the first branch pipe 422. One end of the fourth branch pipe 442 is connected to the second inlet, and the other end of the fourth branch pipe 442 is connected to the second branch pipe 423. In this case, the same pump body 300 can be used for testing the gas relays with different specifications, which can reduce the cost and volume of the above transformer simulation system.

Optionally, a switch control valve 600 is also disposed in the first branch pipe 422 near the junction of the first branch pipe 422 and the third branch pipe 441, and a switch control valve 600 is also disposed in the third branch pipe 441 near the junction of the first branch pipe 422 and the third branch pipe 441. The switch control valve 600 in the first branch pipe 422 is disposed between the second mounting end 421 and the junction of the first branch pipe 422 and the third branch pipe 441. When the insulation oil flows from the first oil pipe 410 to the second oil pipe 420, the switch control valves 600 in the third branch pipe 441 and the fourth branch pipe 442 can be turned off to prevent the insulation oil from flowing back to the oil tank 100 through the third branch pipe 441 or the fourth branch pipe 442. Similarly, when the insulation oil flows from the third oil pipe 430 to the fourth oil pipe 440, the switch control valves 600 in the first branch pipe 422 and the second branch pipe 423 can be turned off to prevent the insulation oil from flowing back to the oil tank 100 through the first branch pipe 422 or the second branch pipe 423.

Specifically, the switch control valve 600 can be a shut-off ball valve, a solenoid valve or a manual ball valve. It is convenient to control the opening and closing of the pipeline.

Further, as shown in FIG. 1, a temperature probe 700 for detecting oil temperature is provided in the oil tank 100, and the temperature probe 700 is disposed at the first outlet. Since the setting temperature of the heating device 200 is not necessarily the same as the temperature of the insulation oil entering the first oil pipe 410, the temperature of the insulation oil entering the first oil pipe 410 can be detected by the temperature probe 700. And the temperature of the heating device 200 can be adjusted according to the temperature detected by the temperature probe 700. In this way, the oil temperature of the insulation oil entering the first oil pipe 410 is close to the oil temperature at the transformer fault, so the setting value of the gas relay can be better measured.

Optionally, the temperature probe 700 is electrically connected to the controller 10. The controller 10 can adjust the heating temperature of the heating device 200 based on the oil temperature in the first oil pipe 410 measured by the temperature probe 700.

Specifically, there may be at least three temperature probes 700 in the oil tank 100, in which one is disposed at the first outlet, one is disposed at the first inlet, and the other is disposed in the region where the heat source 210 is located. It is convenient to fully monitor the temperature of the insulation oil in the oil tank 100.

Further, as shown in FIG. 1, the above transformer simulation system further includes a temperature sensor 800 that is disposed in the first mounting end 411. Thus, the oil temperature of the insulation oil that is about to enter into the gas relay can be detected and the influence of the oil temperature of the insulation oil on the setting value of the gas relay is further understood. Meanwhile, the temperature probe 700 and the temperature sensor 800 are used to understand the temperature changes of the insulation oil, when the insulation oil passes through the first branch pipe 422 from the oil tank 100 to the position near the gas relay.

Optionally, there may be at least two temperature sensors 800, and a temperature sensor 800 is also disposed in an end of the third oil pipe 430 away from the oil tank 100.

Further, as shown in FIG. 1, the first mounting end 411 and the second mounting end 421 are both disposed to be inclined with respect to a horizontal plane, and a central axis of the first mounting end 411 and a central axis of the second mounting end 421 are disposed in a same direction. In a vertical direction, the first mounting end 411 is lower than the second mounting end 421. In this case, the installation of the gas relay in the transformer can be simulated to better simulate the operation environment of the gas relay and obtain a more accurate setting value of the gas relay.

Further, the heating device 200 has a heating temperature in a range from 50° C. to 80° C. When a fault occurs inside the transformer, the oil temperature is generally 50° C.~80° C., so by setting the heating device 200 with the above temperature range, the condition of the insulation oil when the fault occurs can be better simulated.

Further, as shown in FIG. 1, a pressure sensor 900 for detecting oil pressure is provided in the oil tank 100. In this case, the oil pressure of the insulation oil can be measured by the pressure sensor 900, so that the change of the conditions of different insulation oils can be better understood when the temperature rises.

Optionally, there may be at least three pressure sensors 900. One of the pressure sensors 900 is disposed at an end of the first branch pipe 422 near the oil pump. The pressure sensor 900 is disposed at a downstream position of the junction of the first branch pipe 422 and the third branch pipe 441, in the flow direction of the insulation oil. Since the pipe can be switched when testing the gas relays with different specifications, the pressure sensor 900 disposed at the downstream position of the junction of the first branch pipe 422 and the third branch pipe 441, in the flow direction of the insulation oil, may detect a change in the data, such as oil pressure, after the pipe is switched, so as to better understand the condition change of the insulation oil when testing the gas relays with different specifications.

Specifically, the pressure sensor 900, the temperature sensor 800, the first flow sensor 510, the second flow sensor 520, the temperature probe 700, and the like can be used to analyze the data such as flow velocity ratio, temperature ratio, flow rate ratio and power ratio, and the like, of different insulation oils when the pump body 300 with the same power, so as to better understand the working conditions of different insulation oils when the oil temperature rises.

Optionally, as shown in FIG. 1, the pump body 300 includes a mounting cavity 310, a motor 320 and an oil pump wheel connected to the motor 320. The oil pump wheel is disposed in the mounting cavity 310, and the mounting cavity 310 is connected to the first branch pipe 422 and the second branch pipe 423 respectively. The mounting cavity 310 is provided with a pressure detector, a flow velocity detector, a temperature detector and a power detector. In this case, the working condition of the pump body 300 can be sufficiently detected to ensure the accurate control of the flow velocity, oil pressure, and the like of the insulation oil.

Optionally, the first oil pipe 410 and the third oil pipe 430 are both provided with a drain outlet for discharging impurities in the oil tank 100, so as to ensure the above transformer simulation device operation stably.

A simulation and measurement method for a setting value is disclosed in an embodiment, which uses the transformer simulation system as described above, and includes the following steps.

The oil inlet of the gas relay is connected to the first mounting end 411, and the oil outlet of gas relay is connected to the second mounting end 421.

The pump body 300 is activated, and the power of the pump body 300 is set as a normal power of transformer.

The heating temperature of the heating device 200 is set as the oil temperature at transformer fault.

The flow velocity in the first oil pipe is measured according to the first flow sensor, that is, the setting value.

According to the above simulation and measurement method for a setting value, after the gas relay is connected to the first oil pipe 410 and the second oil pipe 420 respectively, the power of the pump body 300 is set to a normal power of the transformer (i.e., the power during normal operation of the transformer), and the heating temperature of the heating device 200 is set to the oil temperature of the transformer fault (i.e., the oil temperature at the time that the transform malfunctions). Thus, the internal environment of the transformer at the transformer fault can be simulated. Thus, the flow velocity in the first oil pipe 410 measured by the first flow sensor 510 is the oil flow velocity at the transformer fault. Then the setting value of the gas relay is obtained. When a different type of insulation oil is put into the oil tank 100, the corresponding setting value of the gas relay can be obtained, so as to prevent the original gas relay from not playing the role of the protection due to the different property of the insulation oil, after the insulation oil type is replaced.

Optionally, before the step of connecting the oil inlet of the gas relay to the first mounting end 411 and connecting the oil outlet of the gas relay to the second mounting end 421, the method further includes the following step.

The environment-friendly insulation oil, such as plant insulation oil or synthetic ester insulation oil, is added to the oil tank 100.

In this case, the new type of insulation oil can be tested to understand the corresponding setting value of the gas relay.

The technical features of above-described embodiments may be arbitrarily combined. For the sake of concise description, not all possible combinations of the technical features in the above embodiments are described. However, as long as there is no contradiction between the combinations of these technical features, all the combinations should be considered as the scope of this disclosure.

The above-described embodiments represent only several embodiments of the present disclosure, and the description thereof is more specific and detailed, but is not to be construed as limiting the scope of the disclosure. It should be noted that a number of variations and modifications may be made by those skilled in the art without departing from the spirit and scope of the disclosure. Therefore, the scope of the disclosure should be determined by the appended claims.

What is claimed is:

1. A transformer simulation system, comprising an oil tank, a heating device, a pump body, a first oil pipe, a second oil pipe and a first flow sensor, wherein:
    said heating device is disposed in said oil tank;
    said oil tank is provided with a first inlet and a first outlet, said first outlet is connected to said first oil pipe, and said first inlet is connected to said second oil pipe;
    an end of said first oil pipe away from said oil tank is a first mounting end for being connected to an oil inlet of a gas relay, and an end of said second oil pipe away from said oil tank is a second mounting end for being connected to an oil outlet of the gas relay;
    said pump body is connected to said first oil pipe or said second oil pipe; and
    said first flow sensor is disposed in said first oil pipe;
    wherein said heating device comprises a heat source, a turbine wheel and a driver, said turbine wheel has a vertically disposed axis, said turbine wheel is disposed opposite to said heat source, and said driver is used to drive the turbine wheel to rotate.

2. The transformer simulation system according to claim 1, further comprising a third oil pipe, a fourth oil pipe and a second flow sensor, wherein:
    said oil tank is further provided with a second inlet and a second outlet, said third oil pipe is connected to said second outlet, and said fourth oil pipe is connected to said second inlet;
    an end of said third oil pipe away from said oil tank and an end of said fourth oil pipe away from said oil tank are both used to be connected to said gas relay;
    an inner diameter of said first oil pipe is greater than an inner diameter of said third oil pipe; and
    said second oil pipe and said fourth oil pipe are both provided with a switch control valve, and said second flow sensor is disposed in said third oil pipe.

3. The transformer simulation system according to claim 2, wherein:
    said second oil pipe comprises a first branch pipe and a second branch pipe, an end of said first branch pipe is said second mounting end, an end of said second branch pipe is connected to said first inlet, and another end of said first branch pipe and another end of said second branch pipe are respectively connected to said pump body; and
    the fourth oil pipe comprises a third branch pipe and a fourth branch pipe, an end of said third branch is connected to the gas relay, another end of said third branch is connected to said first branch pipe, an end of said fourth branch pipe is connected to said second inlet, and another end of said fourth branch is connected to said second branch pipe.

4. The transformer simulation system according to claim 1, wherein a temperature probe for detecting oil temperature is disposed in said oil tank, and said temperature probe is disposed at said first outlet.

5. The transformer simulation system according to claim 4, further comprising a temperature sensor disposed in said first mounting end.

6. The transformer simulation system according to claim 1, wherein said first mounting end and said second mounting end are both disposed to be inclined with respect to a horizontal plane, and a central axis of said first mounting end and a central axis of said second mounting end are disposed in a same direction; and
    said first mounting end is lower than said second mounting end in a vertical direction.

7. The transformer simulation system according to claim 1, wherein said heating device has a heating temperature in a range from 50° C. to 80° C.

8. The transformer simulation system according to claim 1, wherein a pressure sensor for detecting oil pressure is disposed in said oil tank.

9. A simulation and measurement method for a setting value, using the transformer simulation system according to claim 1, comprising:
    connecting the oil inlet of said gas relay to said first mounting end, and connecting the oil outlet of gas relay to said second mounting end;
    activating said pump body, and setting a power of said pump body as a normal power of a transformer;
    setting said heating temperature of said heating device as an oil temperature at a time of a transformer fault; and
    measuring a flow velocity in said first oil pipe according to said first flow sensor, as the setting value.

10. A transformer simulation system, comprising an oil tank, a heating device, a pump body, a first oil pipe, a second oil pipe and a first flow sensor, wherein:
    said heating device is disposed in said oil tank;
    said oil tank is provided with a first inlet and a first outlet, said first outlet is connected to said first oil pipe, and said first inlet is connected to said second oil pipe;
    an end of said first oil pipe away from said oil tank is a first mounting end for being connected to an oil inlet of a gas relay, and an end of said second oil pipe away from said oil tank is a second mounting end for being connected to an oil outlet of the gas relay;
    said pump body is connected to said first oil pipe or said second oil pipe; and
    said first flow sensor is disposed in said first oil pipe; and
    wherein the system further comprises:
    a third oil pipe, a fourth oil pipe and a second flow sensor, wherein:
    said oil tank is further provided with a second inlet and a second outlet, said third oil pipe is connected to said second outlet, and said fourth oil pipe is connected to said second inlet;

an end of said third oil pipe away from said oil tank and an end of said fourth oil pipe away from said oil tank are both used to be connected to said gas relay;

an inner diameter of said first oil pipe is greater than an inner diameter of said third oil pipe; and said second oil pipe and said fourth oil pipe are both provided with a switch control valve, and said second flow sensor is disposed in said third oil pipe.

* * * * *